United States Patent [19]

Yanashima et al.

[11] Patent Number: 4,787,395
[45] Date of Patent: Nov. 29, 1988

[54] BLOOD FLOW MEASURING APPARATUS

[75] Inventors: Tadahiko Yanashima, Fujisawa; Shinichi Amemiya; Ikuo Watanabe, both of Yokohama; Hirohide Miwa, Kawasaki, all of Japan

[73] Assignee: Fujitsu Limited, Kanagawa, Japan

[21] Appl. No.: 826,704

[22] Filed: Feb. 6, 1986

[30] Foreign Application Priority Data

Feb. 8, 1985 [JP] Japan .................. 60-022909

[51] Int. Cl.⁴ ............................................. A61B 10/00
[52] U.S. Cl. .............................. 128/661.09; 73/861.25
[58] Field of Search ........................ 128/660, 661, 663; 73/861.75

[56] References Cited

U.S. PATENT DOCUMENTS

| | | | |
|---|---|---|---|
| 4,141,347 | 2/1979 | Green et al. | 128/663 |
| 4,398,540 | 8/1983 | Takemura et al. | 128/661 X |
| 4,423,737 | 1/1984 | Yono et al. | 128/661 |
| 4,501,277 | 2/1985 | Hongo | 128/663 X |
| 4,501,279 | 2/1985 | Seo | 128/663 |
| 4,509,525 | 4/1985 | Seo | 128/663 |
| 4,622,977 | 11/1986 | Namekawa et al. | 73/861.25 |

Primary Examiner—Francis J. Jaworski
Attorney, Agent, or Firm—Armstrong, Nikaido, Marmelstein & Kubovcik

[57] ABSTRACT

A blood flow measuring apparatus provides a two-dimensional blood stream flow velocity distribution diagram which displays a two-dimensional blood stream flow velocity distribution in a region of a living body to be examined and a one-dimensional blood stream flow velocity distribution diagram which displays a one-dimensional blood stream flow velocity distribution in a linear region specified by a line on the examined region with a measuring condition different from the measurement of the two-dimensional blood stream flow velocity distribution. In the present invention, the two-dimensional blood stream flow velocity diagram and the one-dimensional blood stream flow velocity diagram are simultaneously displayed in such a manner that the corresponding portions can be clearly read, and thus the blood stream flow velocity in each portion can be correctly and easily determined.

5 Claims, 7 Drawing Sheets

BLOOD FLOW MEASURING APPARATUS

BACKGROUND OF THE INVENTION

1. Field of the Invention

The present invention relates to a blood flow measuring apparatus in which a blood stream flow velocity in organs of a human body, especially the heart, is visualized and is displayed with an ultrasonic wave image of an organ. The hemodrometer being particularly effective in carrying out a rapid and correct diagnosis of heart disease.

2. Description of the Related Art

An ultrasonic wave is transmitted into a human body and a reflected wave is received and displayed on a Braun tube, thereby obtaining an image of a particular organ of the human body. Such an apparatus (i.e., an ultrasonic wave diagnosis apparatus) is widely used in the diagnosis and treatment of diseases in the human body. When the ultrasonic wave is impinged onto a moving target such as the blood and is reflected therefrom, deviation of a frequency of the reflected ultrasonic wave by a Doppler signal causes a deviation in the value corresponding to the blood stream flow velocity from a transmitting frequency. A blood stream flow velocity (i.e., a flow velocity component in the sending and receiving directions of the ultrasonic wave) can be obtained by the above deviation, and the blood stream flow velocity distribution can be displayed on the Braun tube. When a disease affecting, for example, the valves of the heart, is present, the blood stream in the heart is in an abnormal state, and therefore, a disease of the heart can be correctly and easily diagnosed by observing the blood stream flow velocity distribution diagram displayed on the Braun tube.

A one-dimensional blood stream flow rate distribution display, such as a blood stream flow velocity distribution on a specified line, is displayed as an M mode image having a time axis, and a two-dimensional blood stream flow velocity distribution display such as a blood stream flow velocity in an organ is displayed as a B mode image.

In the one-dimensional blood stream flow velocity distribution display, the blood stream flow velocity is displayed as a variation in brightness or as a color modulation, or as a graph. In the two-dimensional blood stream flow velocity distribution display, the blood stream flow velocity is displayed as a variation in brightness or as a color modulation.

In the one-dimensional blood stream flow velocity distribution display, when the blood stream flow velocity is displayed as a brightness variation or as a color modulation, the blood stream flow velocity itself can be measured with a high accuracy, however, the brightness variation or color modulation cannot be read with a high accuracy, and it is difficult to determine the spatial position of the organ being measured. When the blood stream flow velocity is graphically displayed in the one-dimensional blood stream flow velocity distribution display, the blood stream flow velocity can be read with a high accuracy, however, it is difficult to determine the position of the organ being measured.

In the two-dimensional blood stream flow velocity distribution display, it is easy to determine the position of the organ being measured but the measurement accuracy is low, and if an increase in the measurement accuracy is desired, one scanning line must be transmitted and received many times, which increases the time necessary to obtain one complete picture.

SUMMARY OF THE INVENTION

An object of the present invention is to provide a blood flow measuring apparatus in which the one-dimensional blood stream flow velocity distribution and the two-dimensional blood stream flow velocity distribution are simultaneously displayed on a display surface.

Another object of the present invention is to provide a blood flow measuring apparatus with which the blood stream flow velocity can be measured correctly and rapidly.

A further object of the present invention is to provide a blood flow measuring apparatus with which diagnosis of a heart disease can be carried out correctly and rapidly.

According to the present invention, a blood flow measuring apparatus provides a two-dimensional blood stream flow velocity distribution diagram which displays a two-dimensional blood stream flow velocity distribution in a region of a living body under examination and a one-dimensional blood stream flow velocity distribution diagram which displays a one-dimensional blood stream flow velocity distribution, in a linear region specified by a line in the examined region, having a measuring condition different from the measurement of the two-dimensional blood stream flow velocity distribution. A characteristic feature of the present invention is that the two-dimensional blood stream flow velocity diagram and the one-dimensional blood stream flow velocity diagram are simultaneously displayed in such a manner that the corresponding portions can be clearly read, and thus the blood stream flow velocity in each portion can be correctly and easily determined.

Further features and advantages of the present invention will be apparent from the ensuing description with reference to the accompanying drawings to which, however, the scope of the invention is in no way limited.

DESCRIPTION OF THE PREFERRED EMBODIMENTS

The one-dimensional blood stream flow velocity distribution display (hereinafter referred to as a 1D display) such as a blood stream flow velocity distribution on a specified line is displayed as an M mode image having a time axis, and the two-dimensional blood stream flow velocity distribution display (hereinafter referred to as a 2D display) such as a blood stream flow velocity in an organ is displayed as a B mode image.

Figure 1:
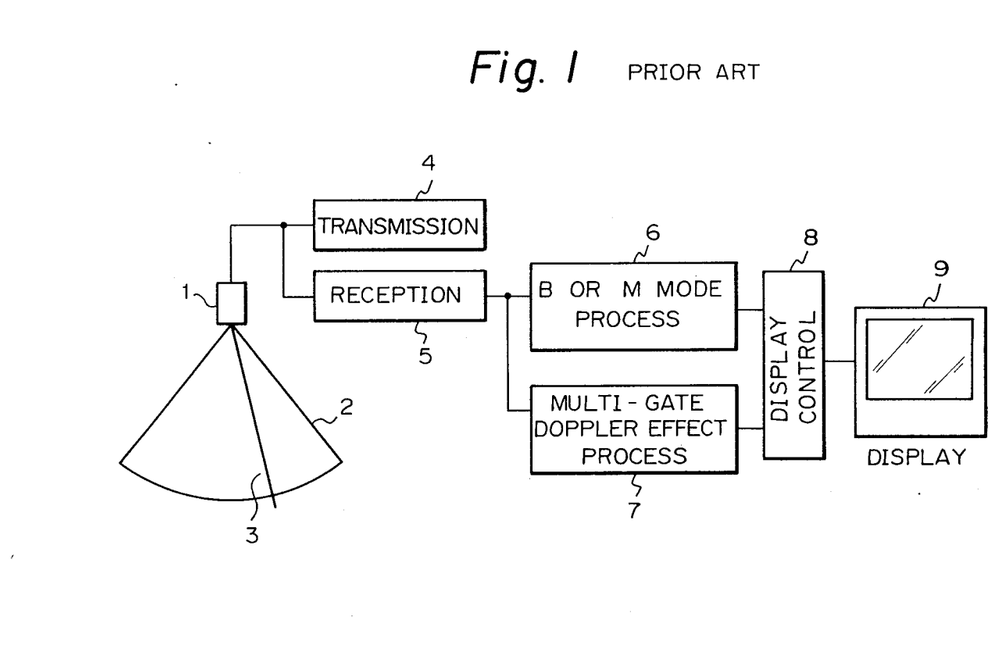
FIG. 1 is a diagram explaining one example of a conventional apparatus.
Figure 2A:
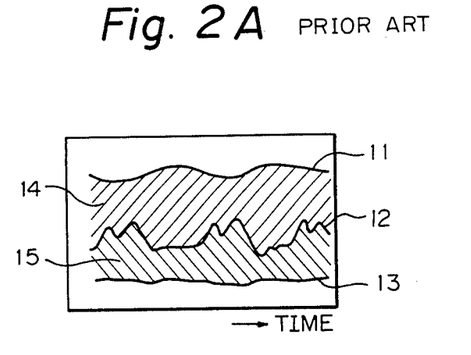
FIGS. 2A and 2B are diagrams explaining the picture displayed by the conventional apparatus of FIG. 1.

FIG. 1 is a block diagram of one example of a conventional apparatus, which will be explained in detail hereinafter. FIG. 2A shows the 1D distribution displayed as an M mode image, wherein the abscissa shows time and the ordinate shows distance (depth). Curves 11, 12, and 13 show movements of the walls of an organ (in this example, a heart), and portions bearing oblique lines show a blood stream flow velocity. That is, each of the curves 11, 12, and 13 shows one point of the wall, the wall moves and therefore the corresponding movement of these points is shown by a locus curve in the time axis. The blood flowing in the space (where the space is linear on a specific line) enclosed by these walls, therefore, has a blood stream flow velocity, and the blood stream flow velocity is designated by a brightness or color modulation. Accordingly, the spaces 14 and 15 show the regions wherein the brightness changes in accordance with the time variation of the blood stream flow velocity in the time axis. In the 1D display, the velocity is designated by a brightness (or color), which makes it difficult to read the value of the flow velocity in any detail.

Figure 2B:
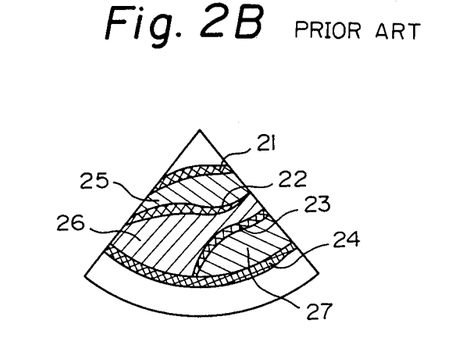

FIG. 2B shows an example of a 2D display as a B mode image, wherein 21~24 show the walls of the organ (the heart), and the portions 25~27 bearing oblique lines show a blood stream flow velocity. This image is obtained by sector-scanning (FIG. 1) an ultrasonic wave in the region 2 to be examined in the human body. The ultrasonic wave is obtained from a probe 1 (an ultrasonic transmitter-receiver) shown in FIG. 1. The ultrasonic wave from the probe 1 is transmitted and the reflected wave is received thereby and, by gradually changing the transmitting angle, the sector region 2 can be scanned by the ultrasonic wave. When the reflected wave is displayed on the Braun tube and is synchronized with the scan, the wall of the organ in the region 2 is shown as 21 to 24 in FIG. 2B; this is known as the B mode image. The blood stream flow velocity between the wall can be obtained by Doppler signal processing of the reflected wave, and is displayed by a brightness or a color modulation. This 2D display can rapidly detect any lesion causing an abnormality in the state of the blood stream in the heart and thus a better diagnosis thereof can be made. However, as the flow velocity is shown by variations in the brightness or the color, the display of the flow velocity is not smooth, for example, in 4 to 8 steps it is difficult to determine the details of the flow velocity.

FIG. 1 shows an outline of a conventional ultrasonic diagnosis apparatus which can display the 1D display or the 2D display. In FIG. 1, the probe is an array type, that is, a plurality of ultrasonic transmitter-receiver elements are assembled as an array. The transmitter-receiver elements of the probe are sequentially selected with a determined phase difference in a transmitter deflection portion 4, and a drive voltage is applied thereto so as to deflect the transmitting angle, whereby the ultrasonic wave is transmitted and scans the sector region 2. A receiver deflection portion 5 sequentially receives the reflected output of the transmitter-receiver element sequentially selected, and sends the same to a B mode or M mode processing portion 6 and a multi-gate Doppler effect processing portion 7. A display control portion 8 provides a picture memory which sends a video signal to a CRT display portion 9. The processing portion 6 writes the B mode or the M mode image data into the picture memory, and the processing portion 7 writes the blood stream flow velocity information (spectrum, means, variance) into the picture memory. Further, as already known, the picture memory stores the same picture (i.e., data) as that displayed on the CRT.

In the M mode image, as shown in FIG. 2A, a linear region is designated which transmits and receives the ultrasonic wave by the cursor 3, the ultrasonic wave is repeatedly transmitted (for example, 100 times) to the same linear region, and the reflected ultrasonic wave is received after each transmission. One of the 100 received data transmission is processed in the M mode in the processing portion 6, written in the picture memory, and displayed on the display portion 9. This process is repeated at every 100 transmissions and receptions of the ultrasonic waves. Then the images depicted by the curves 11, 12 and 13 in FIG. 2A are obtained, in which the abscissa denotes the time and the ordinate denotes the distance to the reflecting point. On the other hand, each set of 100 received data is processed in the Doppler signal processing portion 7 to obtain the blood stream flow velocity, and when this data is written in the picture memory of the display control portion 8, the brightness or the color of the regions 14, 15 is changed in accordance with the blood stream flow velocity, and these changes are displayed. When the ultrasonic wave transmitted and received by the probe is not limited to the same linear region but is scanned over the sector region 2, the image shown in FIG. 2B is obtained.

To obtain the 1D display (i.e., the display in which the flow rate corresponds to the brightness or color, the abscissa shows the time and the ordinate shows the depth, 14 and 15 are also called the flow M), or M mode image (11~13 in FIG. 2A), the transmitting and receiving angle of the ultrasonic wave can be fixed and scanning is not necessary. In this mode, the period for repeating the transmitting and receiving of the ultrasonic wave can be freely set, and the length of the signal to be analyzed can be set to the maximum value of the required time resolution, such as 10~20 mS, so that a precise and stable blood stream flow velocity signal can be obtained. However, scanning is required to obtain a B mode image (2D) and therefore, the number of times that the ultrasonic wave can be transmitted and received in one direction is limited, e.g., 8~16 times (compared to the case of an 1D display of about 64~100 times), and the resolution of the flow velocity is low, e.g., ±4~±8 steps. In both the 1D and 2D displays, a change in the flow velocity is displayed as a change of the brightness or the color and the portion which shows an abnormal blood stream flow velocity can be distinguished from other portions, however, it cannot be quantitatively determined, and thus only a qualitative measurement can be obtained.

Further, in the conventional apparatus, the change from a 1D to a 2D display must be made by a manual switching operation, which is inconvenient.

Moreover, the portion showing a maximum blood stream flow velocity on the 2D display is directly related to a lesion. However, the portion showing this maximum blood stream flow velocity appears only in one portion of the 2D display, and then only for an instant (about 30 mS) of one part of the heart beat period, and thus the problem occurs that it may not be seen even with very careful observation.

Figure 3:
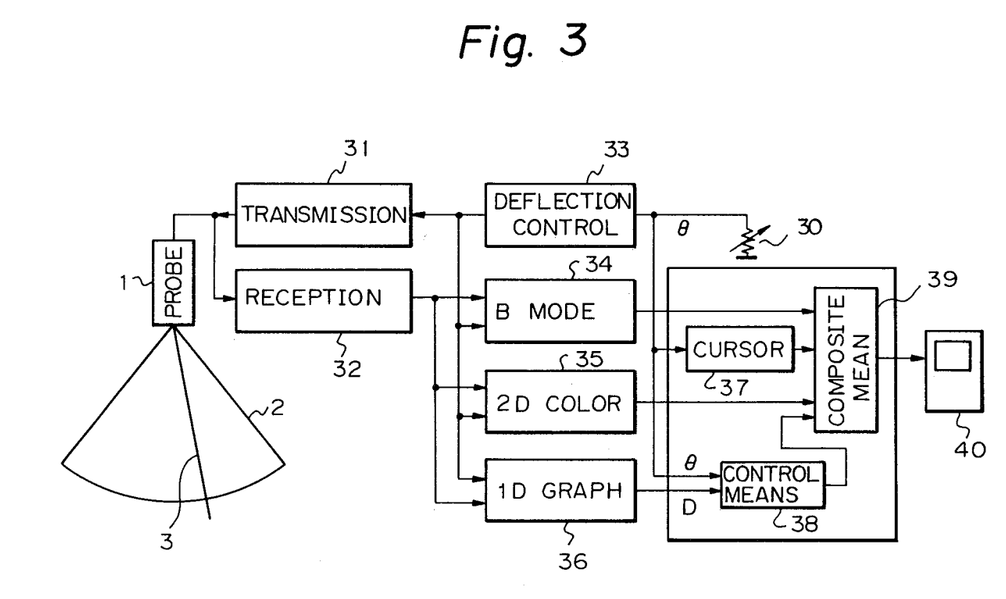
FIG. 3 is a diagram explaining one embodiment of a blood flow measuring apparatus according to the present invention.

FIG. 3 is a diagram of one embodiment of the apparatus according to the present invention. The outline and construction of the apparatus shown in FIG. 3 is similar to that of FIG. 1. In FIG. 3, the data for determining the position of the cursor 3 is supplied as an angle information $\theta$ to a deflection control portion 33 from a cursor position setting means 30 (for example, a variable resistor) provided therein. The data from the probe 1 is supplied via a receiving portion 32 to a B mode processing portion 34, 2D color processing portion 35, and 1D graphic processing portion 36. The output of the deflection control portion 33 is also supplied to the portions 34, 35, and 36. The outputs of the portions 34 and 35 are directly supplied to a composite means 39, and the output of the portion 36 is supplied via a control means 38 to the composite means 39. The angle information $\theta$ is supplied to the control means 38, and is also supplied to a cursor 37 to provide a cursor image data to the composite means 39. The output of the composite means 39 is supplied to a display portion 40. In FIG. 3, the cursor 37 is a picture data generator for showing the cursor line 3. The control means 38 will be explained in detail with reference to FIG. 4.

Figure 4:
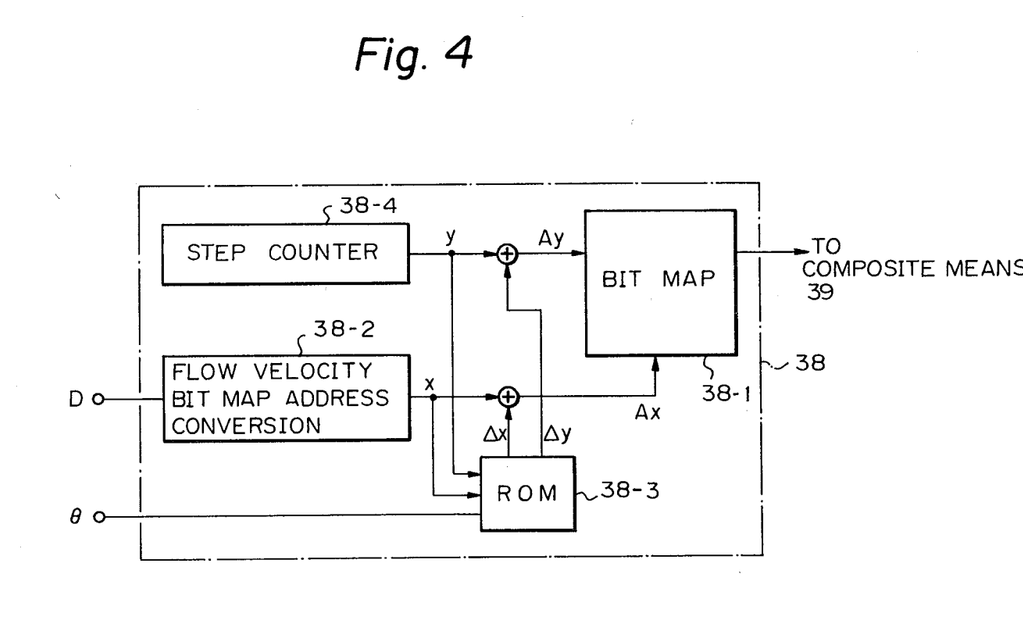
FIG. 4 is a diagram showing an essential portion of the apparatus shown in FIG. 3.
Figure 5A:
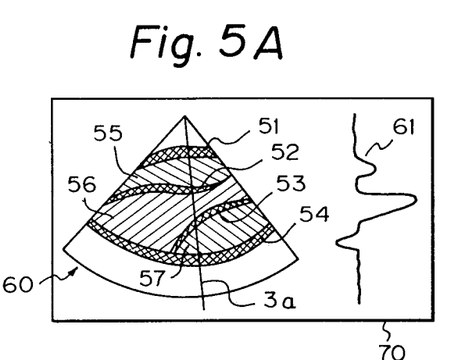
FIGS. 5A, 5B, 5C, and 5D are diagrams explaining the picture displayed by the apparatus shown in FIG. 4.

In FIG. 4, 38-1 shows a bit map (picture memory) wherein the picture data is written from the 1D graphic processing portion 36 shown in FIG. 3. In the present invention, the blood stream flow velocity on the specified line is displayed on a graph (line picture) as shown in FIGS. 5A to 5D. The picture 60 in these drawings is a B mode picture plus the 2D display as shown in FIG. 2B, wherein 3a, 3b, 3c, and 3d designate a cursor which corresponds to a linear region 3 on the region 2 of the scan (region to be examined) shown in FIG. 3. The transmitting and receiving direction of the ultrasonic wave is fixed on the linear region 3 specified by the cursor 3a, 3b, 3c, and 3d, and in this position, transmission and reception are carried out a plurality of times, (in the example mentioned above, 100 times) so that the blood stream flow velocity distribution is determined in the portion 36 and is displayed on the graph of the screen of the display portion (CRT) as the picture 60. In FIG. 5A, the graph is shown as 61, and is displayed side by side with the picture 60. The blood stream flow velocity distribution shown by the graph 61 is, of course, the blood stream line flow velocity distribution in the cursor 3a, which clarifies the correspondence between the one-dimensional display 61 and the two-dimensional display 60.

Figure 5B:
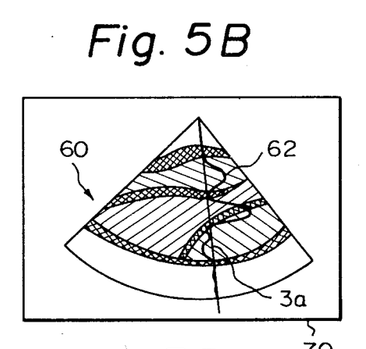
Figure 5C:
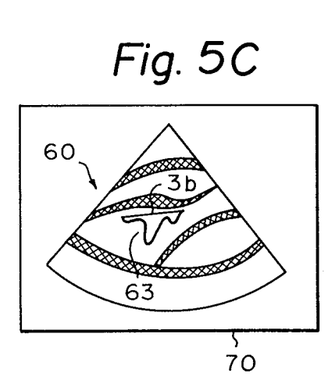
Figure 5D:
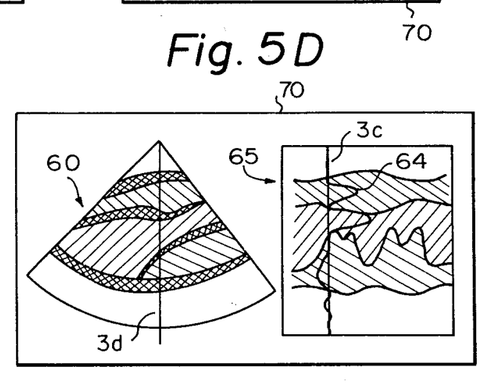

In FIG. 5B, the graph is shown as 62, which is displayed by the cursor 3a in the picture 60, and thus the relationship between the one-dimensional display and the two-dimensional display is clarified. In FIG. 5C, the graph is shown as 63, and is also in the picture 60. The portion of the blood stream line shown by the straight line 3b is displayed as the abscissa of the graph. The straight line 3b can be obtained by connecting the predetermined points of the plurality of cursors, the angle of which is changed sequentially. The cursor 3a is a line showing the transmitting and receiving direction of the ultrasonic wave. Although this cursor is directed only radially, the transmitting and receiving of the ultrasonic wave is carried out along several cursors, the angle of which is sequentially changed, so that when only the blood stream flow velocity on the line 3b is displayed on the graph, the curve 63 is obtained. Herein, the straight line 3b is also called the cursor or the specified line. In FIG. 5D, the graph is shown as 64, and this is displayed on the picture (M mode image plus 1D display) 65. This graph 64 shows the blood stream flow velocity distribution on the cursor 3d in the picture 60, and also shows the blood stream flow velocity at a certain point (this is shown by the abscissa 3c of the graph 64) on the picture 65.

When the graph 62 of FIG. 5B is drawn, the bit map 38-1 corresponds to the picture 70, data of the picture 62 is written in the bit map while converting the coordinate axis thereof. In FIG. 4, D shows the blood stream data of n points (the processing is carried out by such a division) on the cursor 3a. The data D is written in the address which is determined, by the velocity bit address conversion circuit 38-2, on the picture corresponding to the n points, and therefore, on the bit map 38-1. In detail, the data showing the predetermined brightness point is written in the address (i.e., the coordinate of the straight line extending along the direction passing a predetermined x coordinate, when the horizontal direction of the picture is denoted as the x coordinate and the ordinate is denoted as the y coordinate) the direction of which is changed in the x direction by the data D. The address conversion circuit 38-2 outputs such an x coordinate as X and the step counter 38-4 outputs the y coordinate as Y. Step counter 38-4 receives a reset signal from deflection control portion 33 of FIG. 3.

The data of the graph 62 in FIG. 5B can be written in the bit map in substantially the same manner, when the cursor 3a is directed in the y direction (only the x coordinate is different from FIG. 5A). However, when the cursor is directed in the other direction, correction is required. That is, the inclination of the cursor 3a denotes the rotation of the coordinate, and therefore, the coordinate of each point on the graph 62 must be converted in accordance with the rotation of the coordinate. The data necessary for the conversion of the coordinate is stored in a read only memory 38-3. The stored data is read out by the angle information $\theta$ of the cursor, and obtained values $\Delta x$, $\Delta y$ to be corrected are added to the output Y of the step counter 38-4 and the output x of the address conversion circuit 38-2 to provide write addresses Ax and Ay of bright points into the bit map 38-1.

The graph 63 in FIG. 5C can be written in the bit map 38-1 similarly, and thus a detailed explanation thereof is omitted. The display as shown in FIG. 5C is effective when there is a short blood stream flow between the right and left ventricles of the heart, caused by a defect in the wall of the ventricle. This defect is determined and the blood stream flow velocity is measured quantitatively. That is, when the specified line 3b is moved to the region to be examined, to display the graph 63, the defective portion (hole) can be found by the width of the peak portion, and the blood stream flow velocity can be read from the amplitude of the peak portion. In the 2D display, only the brightness is changed, and therefore, a quantitative measurement is difficult. In FIG. 5D, the specified line 3c is placed at a position of the desired timing, for example, the R wave timing, which is important during the period of the heart beat, and the blood stream flow velocity distribution is displayed on the graph at the important point and portion (by the cursor 3d) to enable an exact diagnosis.

To exactly determine the value of the blood stream flow velocity of the point at the maximum blood stream flow velocity on the picture 60, the cursor 3a may be manually moved to that point. However, this can be processed automatically.

Figure 6:
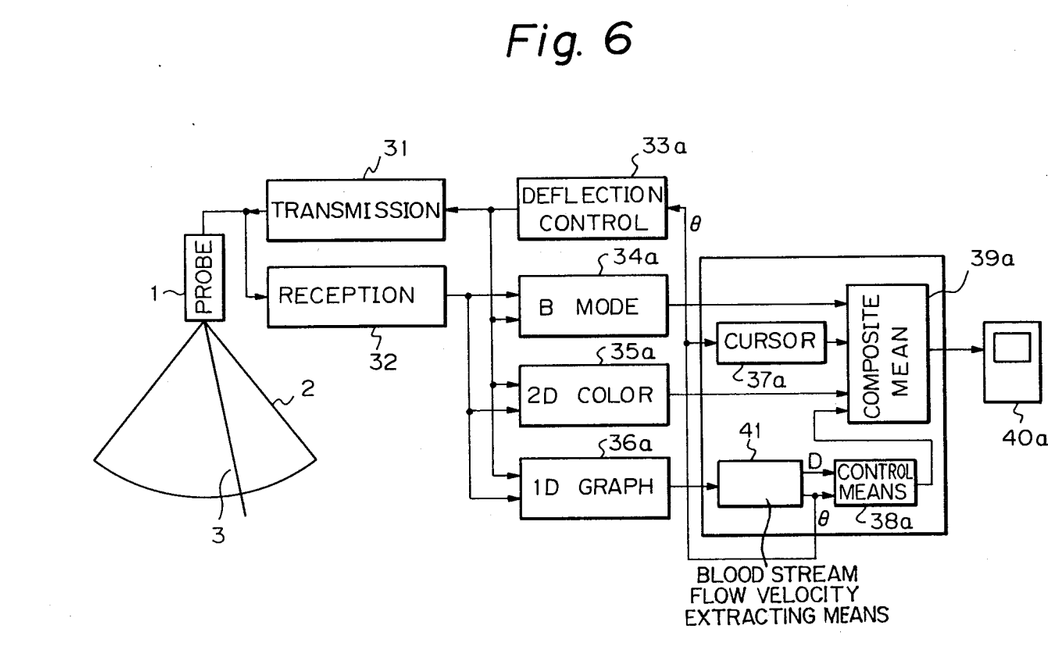
FIG. 6 is a diagram explaining another embodiment of the blood flow measuring apparatus according to the present invention.

FIG. 6 shows a diagram of another embodiment of the present invention. The embodiment shown in FIG. 6 is similar to that shown in FIG. 3, therefore portions corresponding to those in FIG. 3 are shown by the same reference number with a suffix a. In FIG. 6, a blood stream flow velocity extracting means 41 is provided between the 1D graphic processing portions 36a and the control means 38a, and the output angle (θ) information is supplied to the deflection control means 33a and the cursor 37a. Therefore, the cursor position setting means 30 shown in FIG. 3 is not provided.

Figure 7:
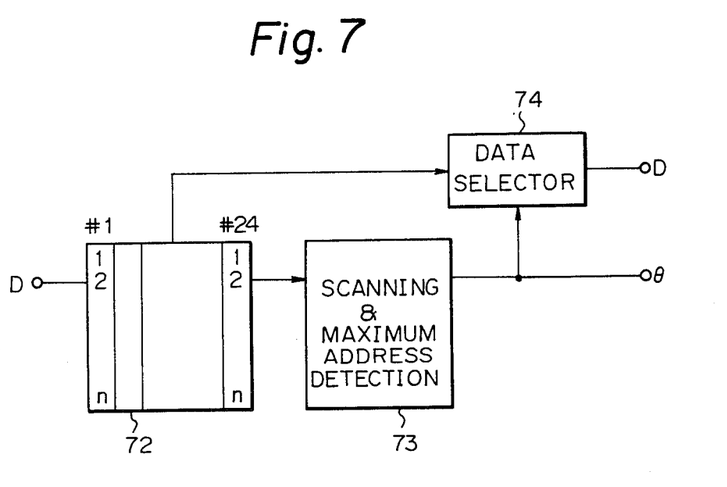
FIG. 7 is a diagram showing an essential portion of the apparatus shown in FIG. 6.

The means 41 will be explained in detail hereinafter. In FIG. 7, the instantaneous blood stream flow velocity data D at n points on the cursor 3a is stored in the memory 72 for every cursor angle, the maximum value of the data set for #1 to #24 is detected at the scanning portion/maximum address detecting portion 73, the data set number having the maximum value is given to a data selector 74, a time sequential data of the number is read via the data selector from the memory 72, and this data (the number is converted to the θ already mentioned) is input as D and θ to the means 38a and to the deflection control 33a, and thus the blood stream flow velocity distribution of the linear region having the maximum blood stream flow velocity can then be displayed on the graph. In addition to the detection of the maximum value, the mean value having a specified value, etc., can be also detected and displayed.

Figure 8A:
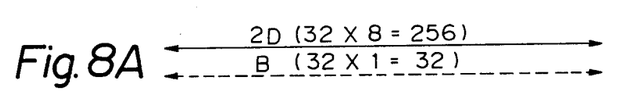
FIGS. 8A to 8C are diagrams explaining the processing time in the apparatus according to the present invention.

To display the linear picture graphs 61 to 64 together with the picture 60 as shown in FIGS. 5A to 5D, the timing relationship must be considered. As the present invention provides an apparatus suitable for determining the movement of the blood in a moving organ such as the heart, the compound display must be carried out in real time. This process time is explained by FIGS. 8A to 8C. Namely, the picture shown in FIG. 5B can be obtained as follows. The ultrasonic wave is transmitted and received 8 times per one direction, Doppler signals are taken out from these signals, and a B mode signal is obtained from the first 8 times of transmitting and receiving. The sector region is divided into 32 directions, and therefore, the number of transmissions and receptions are $32 \times 8 = 256$ times, as shown in FIG. 8A. If the measurement is carried out to a depth of 19.5 cm, the first transmission and reception requires $$19.5 \text{ cm} \times 2/1.5 \times 10^5 \text{ cm} = 260 \ \mu S$$

and thus a total time is required of $$32 \times 260 \ \mu S = 83 \text{ mS}$$

and thus a frames rate is 12 frame per second.

Figure 8B:
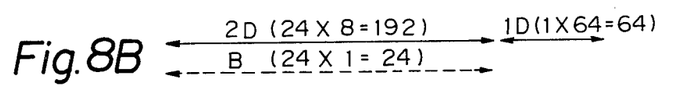
Figure 8C:
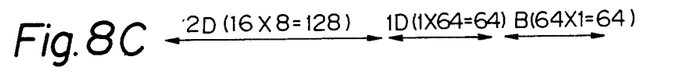

The data of the graphs 61 to 64 may be obtained in other ways, as shown in FIGS. 8B or 8C. That is, in FIG. 8B, the sector region is divided into 24 directions, and therefore the transmission and reception is carried out 192 times for the 2D display, and the remaining transmissions and receptions of $256 - 192 = 64$ times are allocated for the 1D (graph) diaplay. When the number of times of transmission and reception increases, an improvement of the S/N and of the frequency resolution in the flow velocity can be expected. In the graph display for the qualitative measurement, it is preferable to change the measuring condition (i.e., change the number of times of transmission and reception for one direction), and thus the one-dimensional blood stream flow velocity distribution can be measured with a high accuracy. Further, in FIG. 8C, the sector region is divided into 16 directions, whereby a 2D display is carried out by a transmission and reception of $16 \times 8 = 128$ times, and the remaining 128 times are divided in two and allocated for the 1D display and B mode display, respectively.

In FIG. 8B, the sector region is simply divided into 24 directions for the 2D display, the transmission and reception of the ultrasonic wave is carried out 8 times in one direction, and, in the linear region for the 1D display specified by the cursor, the transmission and reception of the ultrasonic wave is continuously carried out 64 times. Then, the transmission and reception for the 2D display is continued. However, the transmission and reception of the ultrasonic wave may be carried out alternatively for the 1D display and the 2D display.

As mentioned above, according to the present invention, an abnormal portion of the blood stream in the human body can be easily and rapidly visualized and quantitatively measured. Therefore, the present invention is very effective for determining the type and size of the lesion, observing the process of the medical treatment, and determining the results of an operation.

We claim:

1. An improved ultrasound blood flow measuring apparatus which includes a first means for measuring in real time a two-dimensional blood sream flow velocity distribution in a region in a living body by transmission and reception of ultrasonic waves along a plurality of scanning lines and providing data representative thereof, and a second means for measuring a one-dimensional blood stream flow velocity distribution of a linear region along a predetermined line from among said scanning lines in said living body region by transmission and reception of ultrasonic waves ad providing data representative thereof; the improvement comprising:

means for simultaneously displaying on a single display screen said one-dimensional and said two-dimensional blood stream data, cursor means for displaying said predetermined line superposed on said living body region data, wherein said second means includes a processor means and a memory means, said processor means for writing blood stream flow velocity information derived from the reception of ultrasonic waves into a picture memory as said one-dimensional flow representative data, and said second means being adapted to measure said one-dimensional blood stream flow velocity distribution along said predetermined line for a first number of times per scan, said first means being adapted to measure said two-dimensional blood stream velocity distribution for a second number of times per scan line of said distribution, per scan, said first number being larger than said second number.

2. A blood flow measuring apparatus according to claim 1, further comprising means for alternately operating measurements of said first means and said second means in a time-divisional manner.

3. A blood flow measuring apparatus according to claim 1, further comprising a detecting means for detecting a specified value from any output of said second means for each living body region, and for displaying said output of said second means detected by said detecting means.

4. A blood flow measuring apparatus according to claim 1, further comprising means for displaying an output of said second means as a change of a one-dimensional blood stream flow velocity distribution on a time axis or as superimposed on a displayed picture, by a variation in brightness or a color change.

5. A blood flow measuring apparatus according to claim 1, further comprising means for displaying a B mode diagram superimposed on a two-dimensional blood stream flow velocity distribution diagram.

* * * * *